United States Patent
Unger et al.

(10) Patent No.: US 6,501,819 B2
(45) Date of Patent: Dec. 31, 2002

(54) MEDICAL DIAGNOSTIC METHOD AND APPARATUS TO CONTROL DUAL ENERGY EXPOSURE TECHNIQUES BASED ON IMAGE INFORMATION

(75) Inventors: Christopher David Unger, Delafield, WI (US); Kenneth Scott Kump, Waukesha, WI (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 22 days.

(21) Appl. No.: 09/739,127

(22) Filed: Dec. 18, 2000

(65) Prior Publication Data

US 2002/0075997 A1 Jun. 20, 2002

(51) Int. Cl.[7] ................................. H05G 1/64
(52) U.S. Cl. ..................... 378/5; 378/98.9; 378/207
(58) Field of Search ............... 378/62, 4, 5, 16, 378/19, 98.9, 98.2, 207

(56) References Cited

U.S. PATENT DOCUMENTS

| | | | | |
|---|---|---|---|---|
| 4,868,857 A | * | 9/1989 | Dobbins, III | 378/98.2 |
| 6,343,112 B1 | * | 1/2002 | Petrick et al. | 378/98.9 |

* cited by examiner

Primary Examiner—Drew A. Dunn
(74) Attorney, Agent, or Firm—McAndrews, Held & Malloy, Ltd.; Peter J. Vogel; Michael A. Dellapenna

(57) ABSTRACT

A preferred embodiment of the present invention provides a method and apparatus for optimized dual energy image acquisition. The system comprises a dual energy medical imaging system, a detector, a user interface, an image segmentation module, a characterization module, and a control module. The method comprises obtaining an image from a first exposure of a patient and segmenting the image into an anatomy of interest. The method further comprises characterizing the segmented anatomy in terms of a set of patient parameters and optimizing a second exposure of the segmented anatomy based upon said anatomy and the characterization of the anatomy. A resulting anatomy image is obtained from analysis of the first and second exposures.

24 Claims, 3 Drawing Sheets

MEDICAL DIAGNOSTIC METHOD AND APPARATUS TO CONTROL DUAL ENERGY EXPOSURE TECHNIQUES BASED ON IMAGE INFORMATION

CROSS REFERENCE TO RELATED APPLICATIONS (if applicable)

Not applicable.

STATEMENT REGARDING FEDERALLY SPONSORED RESEARCH & DEVELOPMENT (if applicable)

Not Applicable.

BACKGROUND OF THE INVENTION

The preferred embodiments of the present invention generally relate to dual energy exposure techniques, and in particular relate to using image information to control dual energy exposure techniques.

X-ray imaging has long been an accepted medical diagnostic tool. X-ray imaging systems are commonly used to capture, as examples, thoracic, cervical, spinal, cranial, and abdominal images that often include information necessary for a doctor to make an accurate diagnosis. X-ray imaging systems typically include an x-ray source and an x-ray sensor. When having a thoracic x-ray image taken, for example, a patient stands with his or her chest against the x-ray sensor as an x-ray technologist positions the x-ray sensor and the x-ray source at an appropriate height. X-rays produced by the source travel through the patient's chest, and the x-ray sensor then detects the x-ray energy generated by the source and attenuated to various degrees by different parts of the body. An associated control system obtains the detected x-ray energy from the x-ray sensor and prepares a corresponding diagnostic image on a display.

The x-ray sensor may be a conventional screen/film configuration, in which the screen converts the x-rays to light that exposes the film. The x-ray sensor may also be a solid state digital image detector. Digital detectors afford a significantly greater dynamic range than conventional screen/film configurations.

One embodiment of a solid state digital x-ray detector may be comprised of a panel of semiconductor Field Effect Transistors (FETs) and photodiodes. The FETs and photodiodes in the panel are typically arranged in rows (scan lines) and columns (data lines). A FET controller controls the order in which the FETs are turned on and off. The FETs are typically turned on, or activated, in rows. When the FETs are turned on, charge to establish the FET channel is drawn into the FET from both the source and the drain of the transistor. The source of each FET is connected to a photodiode. The drain of each FET is connected to readout electronics via data lines. Each photodiode integrates the light signal and discharges energy in proportion to the x-rays absorbed by the detector. The gates of the FETs are connected to the FET controller. The FET controller allows energy discharged from the panel of photodiodes to be read in an orderly fashion. The readout electronics convert the energy discharged from photodiodes to electrical signals. The energy discharged by the photodiodes in the detector and converted by the readout electronics is used by an acquisition system to activate pixels in the displayed digital diagnostic image. The panel of FETs and photodiodes is typically scanned by row. The corresponding pixels in the digital diagnostic image are typically activated in columns.

The FETs in the x-ray detector act as switches to control the charging of the photodiodes. When a FET is open, an associated photodiode is isolated from the readout electronics and is discharged during an x-ray exposure. When the FET is closed, the photodiode is recharged to an initial charge by the readout electronics. Light is emitted by a scintillator in response to x-rays absorbed from the source. The photodiodes sense the emitted light and are partially discharged. Thus, while the FETs are open, the charge on the photodiodes moves to a charge level representative of the x-ray dose. When a FET is closed, a desired voltage across the photodiode is restored. The measured charge amount to re-establish the desired voltage becomes a measure of the x-ray dose integrated by the photodiode during the length of the x-ray exposure.

X-ray images may be used for many purposes. For instance, internal defects in a target object may be detected. Additionally, changes in internal structure or alignment may be determined. Furthermore, the image may show the presence or absence of objects in the target. The information gained from x-ray imaging has applications in many fields, including medicine and manufacturing.

A common type of cancer today in the United States is lung cancer. Lung cancer is fatal at an extremely high percentage of the time when not detected early enough. However, no good screening process is known to exist. One proposal is to use CT (computed tomography) systems to screen for lung cancer. However, the cost and dosage for a screening application may be prohibitive.

"RAD" is a term that denotes single shot radiography. For example, a typical chest film taken at a hospital is taken with a RAD system. X-rays for broken bones are also often taken with RAD systems. Digital RAD systems are typically cheaper and use less dosage for an examination than CT systems. Additionally, the staging requirements (especially floor space) are less as well, simplifying the concept of a dedicated screening room.

However, conventional RAD systems do not have the discrimination needed to see lung cancer nodules at an early stage of development even though RAD systems produce high resolution images. The lung cancer nodules are high contrast (compared to air), and, thus, a dominant issue for RAD systems is fixed pattern background noise (i.e., the ribs) present in an x-ray image. A technique called dual energy can separate the soft tissues from the bones creating 2 output images. The soft tissue image has the structured background noise removed. Dual energy allows one to view the cancer nodules without the ribs, allowing the nodules to stand out clearly against the soft tissue.

An alternative imaging technique to dual energy exposure is a CR (computed radiography) system. A CR system has a detector with two detector areas. In a CR system, a first detector is located behind a second detector. In a CR type system, only one exposure is taken by the two detectors. Since only one exposure is taken, a CR type system may reduce the energy exposure dosage that a patient receives. One drawback of a CR system is that the second detector exhibits very high noise. The second detector also only allows a low exposure. As a result, the difference in energies between the two detector images is limited. In other words, there is very low discrimination between the detector images. In order to get a sufficiently high separation in exposure energies and a sufficiently high signal-to-noise ratio (SNR) for the second (high x-ray energy) image, the patient dose would be excessive.

Conventional RAD systems have been proposed that operate based on the concept of dual energy, in accordance with which a system that takes two exposures, one low energy and one high energy, to separate the soft tissue (a low energy absorber) from the bone (a high energy absorber). The second exposure deposits extra dose to the patient, and therefore it is desirable to adjust the second exposure dependent on the patient characteristics. In addition image quality can be optimized by regulating the proportion of dose between the 2 exposures.

A need remains for a system that uses anatomical information in an image to control and adjust the parameters for the second exposure.

BRIEF SUMMARY OF THE INVENTION

A preferred embodiment of the present invention provides a method and apparatus for dual energy image acquisition. The method comprises obtaining an image from a first exposure of a patient and segmenting the image into an anatomy of interest. The method further comprises characterizing the segmented anatomy in terms of a set of patient parameters and adjusting exposure characteristics for a second exposure of the segmented anatomy based upon the set of patient parameters and the characterization of the anatomy. The resulting anatomic images are obtained from analysis of the first and second exposures. In an alternative embodiment, said first exposure may be a low dose scout exposure. Then the $2^{nd}$ and $3^{rd}$ exposure would be optimize and used for the subsequent dual energy decomposition. In a preferred embodiment, the set of patient parameters may include attenuation of the segmented anatomy, normalized patent data, and a mathematical model of the segmented anatomy.

A preferred embodiment of the system comprises a dual energy medical imaging system, a detector, a user interface, an image segmentation module, a characterization module, and a control module. The dual energy medical imaging system is adjustable for various exposure dosage levels and techniques. In an alternative embodiment, the dual energy medical imaging system may be adjusted for a low dose scout exposure. In a preferred embodiment, the dual energy medical imaging system adjusts between a first exposure dosage level and a second exposure dosage level. The detector converts exposure energy into digital signals. In a preferred embodiment, the exposure energy comprises x-ray energy. The interface allows a user to set image acquisition parameters. The image segmentation module identifies an anatomy of interest. The characterization module characterizes the anatomy of interest according to a set of patient parameters. The control module optimizes the subsequent dual energy image acquisition. In a preferred embodiment, the system further comprises an output for displaying the resulting anatomy images.

DETAILED DESCRIPTION OF THE INVENTION

Figure 1:
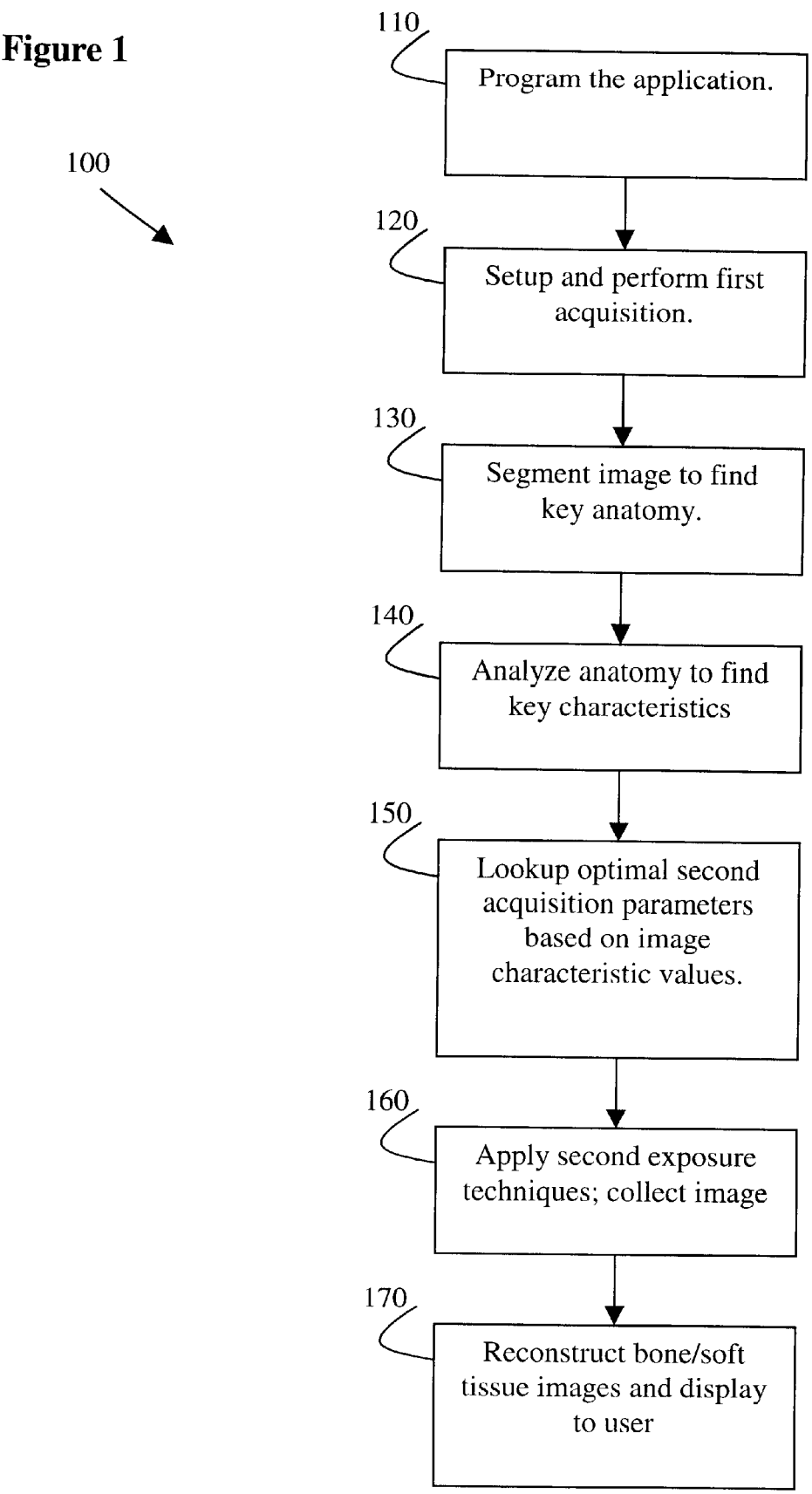
FIG. 1 illustrates a preferred embodiment of a method for adjusting dual energy image acquisition.

FIG. 1 illustrates a preferred embodiment of a method 100 for dual energy image acquisition. In step 110, a user selects dual image acquisition on a medical diagnostic imaging system. In a preferred embodiment, the selecting step involves choosing an anatomy of interest (such as chest, legs, head, and the like). The user may be a technician operating the system in real-time. Alternatively, the user may pre-program the system. The system may execute the pre-programmed sequence.

In step 120, a first image acquisition is taken using default exposure settings. In a preferred embodiment, the default exposures are taken with exposure parameters pre-set for particular regions of interest (chest, head, etc.) and patient body size (small child, medium woman, large man). The range of x-ray energy with default exposure settings ranges between 50 kVp (kilo-volts, x-ray beam voltage) and 150 kVp.

In a preferred embodiment, the first image acquisition is stopped using automatic exposure control (AEC). Using automatic exposure control devices (rather than manual exposure control and the like) may decrease patient exposure and may also reduce the chance of inaccurate patient exposure. With manual exposure control, a technician sets exposure peak voltage (kVp), mA (milliamps of x-ray beam current), and exposure duration (msec). The exposure ends when the time is expired. For automatic exposure control, the kVp and mA are input into the system, but the system determines the duration of the exposure. The exposure ceases when the exposure output has reached an appropriate level. The AEC device converts exposure energy into an electrical signal used to end the exposure when the exposure output reaches the appropriate level (and thus the electrical signal reaches an appropriate level). The exposure time may vary depending on the object being imaged (for example, thicker objects may take longer to image than thinner objects). Additionally, for example, in a lung cancer screening, short exposures are desirable to minimize motion (heart and breathing) and to improve image registration. In a lung cancer screening, it is desirable to have no bone shadow in the tissue image.

In an alternative embodiment, a low dose "scout" view image is used to position the patient. The "scout" view may be a poor signal to noise ratio image showing what internal organs are covered by a scan of a patient. The "scout" view may also show alignment of the internal organs. The low dose "scout" image may serve as the first image acquisition, but is generally used to estimate patient/organ thickness which is used to optimize the two subsequent dual energy images. The scout image typically utilize <5% of total dose.

Figure 3:
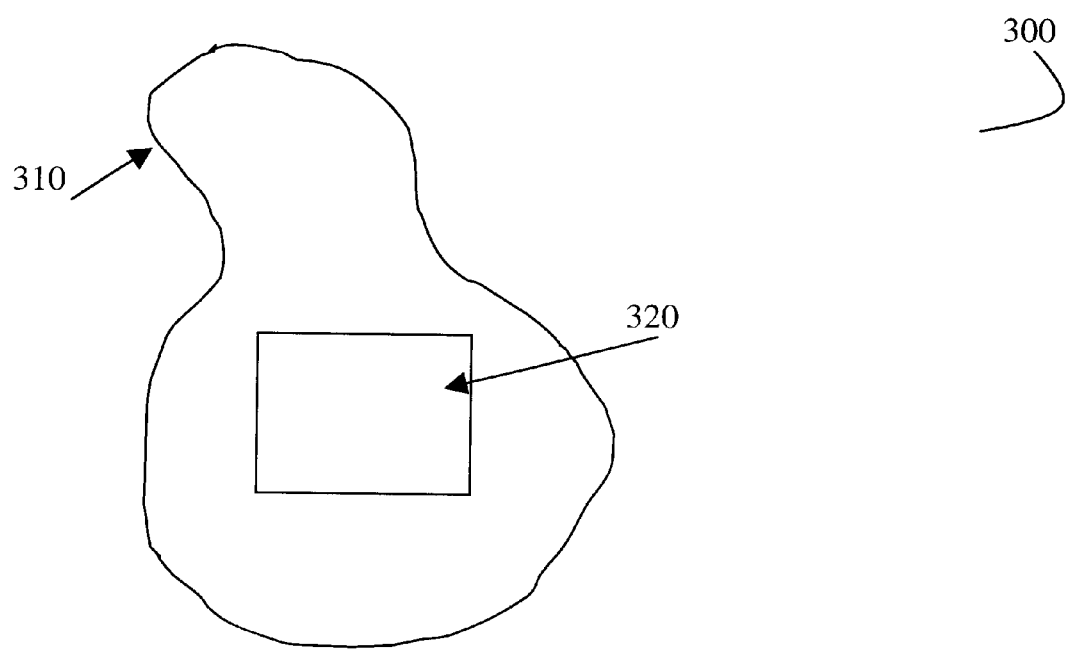
FIG. 3 illustrates a medical diagnostic image of an anatomy.

In step 130, a medical diagnostic image resulting from the first image acquisition is segmented to find an anatomy of interest. In a preferred embodiment, the first medical diagnostic image is segmented by an automatic algorithm which identifies the anatomy of interest and retains the portion of the first medical diagnostic image corresponding to the anatomy of interest. The anatomy of interest may be identified based upon information supplied by the user (or a pre-programmed routine). Using user input, standard information about patient anatomies, and the like, the anatomy of interest may be identified in the first medical diagnostic image. FIG. 3 illustrates a medical diagnostic image 300 resulting from the first image acquisition. In a preferred embodiment the image 300 comprises an image acquisition 310 of a patient. The patient image acquisition 310 comprises an anatomy of interest 320. The image 300 may be segmented to isolate the anatomy of interest 320. In segmentation, the system focuses on the area surrounding the anatomy of interest 320, and the rest of the image may be ignored. As an example, the throat/larynx and spine form a patient segment of interest for a neck image acquisition.

The area of the first medical diagnostic image comprising the throat, larynx, and spine is identified as the segment of interest in the image. The system focuses on the segment of the medical diagnostic image comprising the throat, larynx, and spine in analyzing a neck image. As an example, the lungs and diaphragm form a segment of interest in a patient image for a chest image acquisition. The segment of the medical diagnostic image comprising the lungs and diaphragm is identified and the segment of interest for a chest image acquisition.

In step 140, the anatomy of interest is analyzed to identify at least one of a set of anatomy image characteristics, such as patient thickness. The characteristics may be used to characterize the anatomical segments 320 of interest. The anatomical segments 320 of interest may be characterized in terms of patient parameters, such as the attenuation of the segments. Patient parameters may also include the brightest and darkest regions of the anatomy of interest. The analysis in step 140 may also include correlating current data with a normalized patient and/or using a mathematical model of the anatomy of interest to characterize parameters.

In step 150, second image acquisition parameters are selected based on the characteristics of the anatomy 320 of interest. The second image acquisition parameters or settings are used to adjust the x-ray acquisition techniques visualization, and/or clarity of the anatomy 320 and pathology of interest, while minimizing dose. For example, the kVp (x-ray energy, kilo-volt energy of x-ray beam) and spectral filters may be selected to optimize the bone/soft tissue separation at the segment of interest. The mAs (milliamps times seconds) and x-ray detector gain may be chosen to minimize dose while maintaining a sufficient signal in the most dense area of the segment of interest.

In step 160, the second image acquisition parameters or settings are used to obtain a second image acquisition. A second resulting image is collected. In step 170, bone and soft tissue images are reconstructed and displayed. The resulting image may be output on a monitor. The resulting image may also be stored in a memory.

Figure 2:
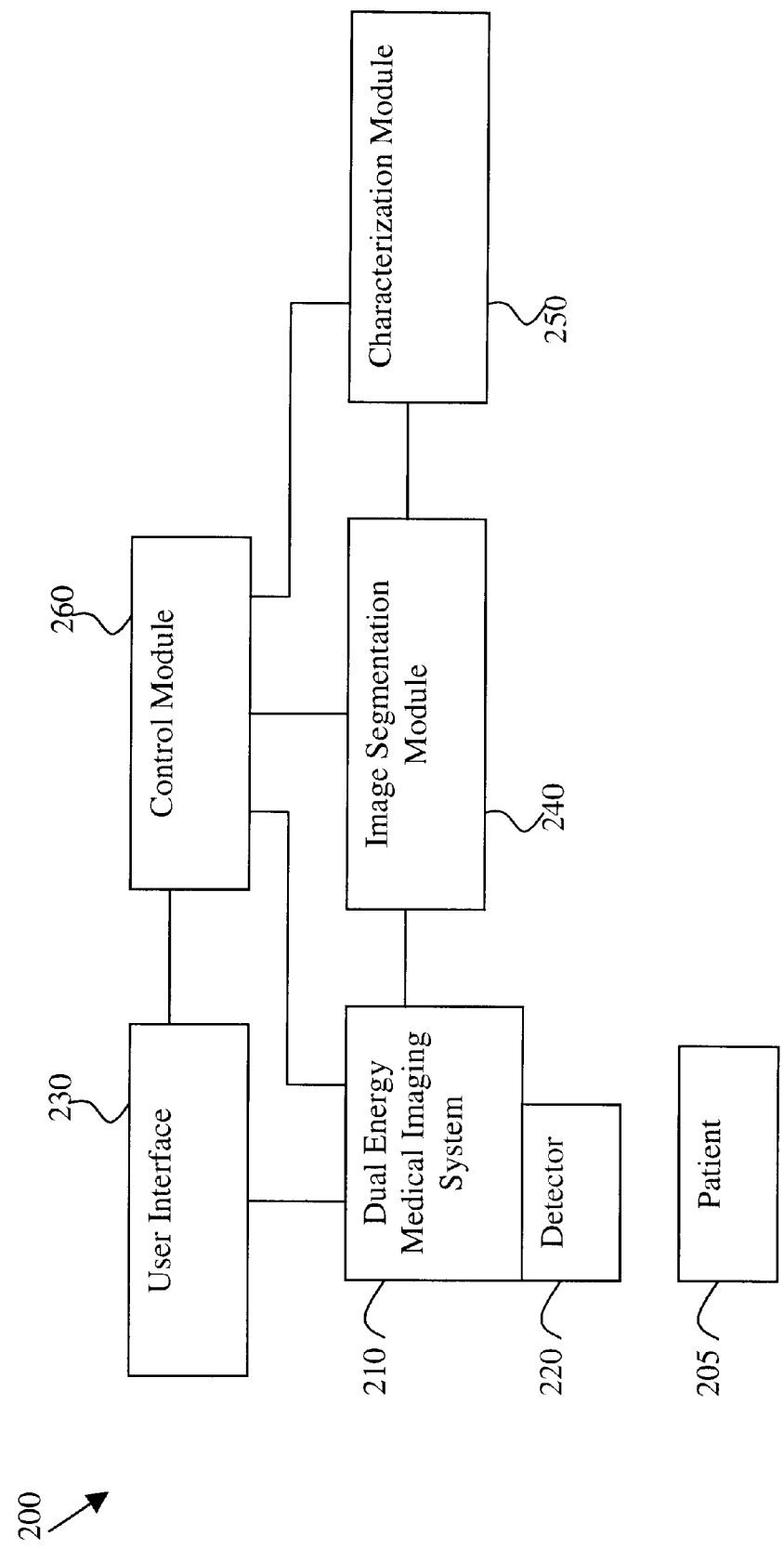
FIG. 2 illustrates a system for adjusting dual energy image acquisition.

FIG. 2 illustrates a system 200 for optimizing dual energy image acquisition. The system 200 for optimizing dual energy image acquisition comprises a patient 205 and a dual energy medical imaging system 210. The dual energy medical imaging system 210 comprises a detector 220, a user interface 230, an image segmentation module 240, a characterization module 250, and a control module 260. In a preferred embodiment, the dual energy medical imaging system 210 may be adjusted quickly for changes in imaging techniques.

The detector 220 converts x-rays to digital signals. Preferably, the detector 220 is a solid state detector. The detector 220 may adjust its operation very quickly (maximum 1 second). The dual energy medical imaging system 210 employs the detector 220 to produce an image 300 based on energy, such as x-ray energy, transmitted through the patient 205.

The user interface 230 allows a user to input configuration information. The configuration information may include information such as a disease or an anatomical region to be addressed. The dual energy medical imaging system 210 may be configured based on the user input from the user interface 230.

The image segmentation module 240 receives an image 300 of the patient 205 from the dual energy medical imaging system 210 with detector 220. The image segmentation module 240 identifies an anatomical region 320 of interest in the patient 205. An anatomical region 320 of interest includes a chest, lung, heart, brain, arm, leg, neck, and the like. The image segmentation module 240 identifies an anatomical region 320 of interest in the patient 205 based upon information from the user interface 230. The image segmentation module 240 may also use standard patient anatomy information to identify the anatomical region 320 of interest in the patient image 300. For example, a user may configure the system 200 for a chest image acquisition. The image segmentation module 240 uses the user's selection of a chest scan with information on the parameters of a standard chest scan to identify the portion of the patient image 300 that corresponds to the lungs, diaphragm, and the like (components of a chest area image).

Image segmentation is the process of identifying different spatial regions in an image. Image segmentation may be an anatomically specific process because image segmentation is preferably adjusted for each region in the body. Different regions (anatomies) in a patient may have different patient parameters and different image characteristics, such as the composition, size, thickness, and distribution of anatomical and/or foreign objects. For example, in a chest image, there are lungs, spine, diaphragm, neck, shoulders, ribs, etc., each with a specific size, density, composition, and position. Image segmentation may be adjusted for different regions of the body based on analyses of those regions.

A preferred segmentation method utilizes a mixture of spatial and statistical algorithms. The collimator and raw radiation areas are removed using morphological operations, such as dilation and erosion operations with pre-selected kernel sizes. Next, the anatomical contents are delineated using a gradient filter which identifies boundaries. With a gradient image, the edges or object boundaries are assigned a high absolute value, and flat areas are assigned a value of 0. An edge-strength threshold is calculated based upon the x-ray system patient input dose and the expected (heuristic) values based upon the patient anatomy. For example, an image threshold may be calculated based on an estimate of noise in the image (such as by using standard deviation in a flat region) divided by the patient input dose times a scalar which depends upon the anatomy. The output is a set of non-rectangular regions of interest, presumably from different anatomical features. The image is now segmented.

In an alternative embodiment, the image is segmented into 10×10 anatomical regions of interest, and image thresholds and characteristics are calculated for each of the regions. The dose level from the dual energy medical imaging system 210 may also be used to predict or confirm an image threshold level.

The characterization module 250 receives at least a segment 320 of the patient 205 from the image segmentation module 240. The characterization module 250 characterizes the segment 320 of anatomy found by the image segmentation module 240. In a preferred embodiment, the segment 320 is characterized in terms of a set of patient parameters. The set of patient parameters includes image attenuation, normalized patient data, mathematical model of anatomy, image area brightness, image area darkness, and the like that are calculated based upon each segmented region's graylevel distribution. The image data of the anatomical segment 320 is correlated with the set of patient parameters. In a preferred embodiment, the set of patient parameters may be specified by information from the user interface 230.

Features in an x-ray image generally comprise a map of a line integral of x-ray attenuations along the path of x-ray energy. For a dual energy imaging technique, patient thickness may be estimated. In a preferred embodiment, the x-ray input may be determined via feedback from an x-ray source. The detected x-ray output may be measured once the x-rays have penetrated the patient. The equivalent patient thickness (in 2D) may be calculated for every pixel detected in the image. $I=I_0\exp(-u*x)$, where $I_0$ is incident x-ray exposure, u is an attenuation coefficient, x is patient thickness, and I is output x-ray exposure. In a preferred embodiment, an attenuation coefficient is assumed that matches the "average" tissue, for example, water. By rearranging the equation, x may be calculated. A map of patient thickness may be calculated using $x=-\ln(I/I_0)/u^*$, where $u^*$ is the assumed attenuation coefficient.

In order to normalize patient data, "median" patient attenuation maps may be developed for areas of interest (chest, abdomen, pelvis, etc.). Preferably, the "median" patient attenuation maps represent the $50^{th}$ percentile of people. In an exposure, the acquired patient map is compared to a corresponding median map for the area of interest. In a preferred embodiment, comparison of the maps is done by simple division. Numerical results greater than 1.0 indicate the patient anatomy is thicker than the median value. Numerical results less than 1.0 indicate the patient anatomy is thinner than the median value. Comparison of the maps may also be accomplished by segmenting the image into regions and dividing image region statistics. For example, a chest image may be segmented into a right lung region, left lung region, diaphragm region, neck region, head region, spine region, and, perhaps, background. The mean thickness in each region may be computed. Each region's mean thickness may be divided by the "median patient" data.

For a mathematical model of an anatomy, a two-dimensional mathematical equation is computed and the parameters of the resulting mathematical model are fit to the new patient thickness data. An example of a mathematical model includes a 2D polynomial. In a preferred embodiment, N normalized values are stored for the anatomical region of interest. Preferably, the patient image is segmented and normalized anatomical region of interest thickness values are computed.

For characterization of the segmented image, the normalized thickness data may be input into an equation or look up table to calculate kVp (kilo-volts, x-ray beam voltage) and mAs (milliamps times seconds, x-ray beam current). Preferably, the look up table comprises a pre-defined range of input thicknesses and imaging technique values. In a preferred embodiment, the look up table values are obtained using x-ray calibration phantoms and clinical trials designed to adjust the contrast-to-noise ratio per patient dose. Alternatively, an equation may be used to calculate the desired values. For example, $kVp=A\#P$, where A is a 1×N adjustment matrix and P is a N×1 model parameter matrix. Alternatively, P may be a N×1 matrix of thickness values for anatomical regions of interest taken from the normalized thickness values. From mAs, mA (milliamps) and an image focal spot may be calculated. In a preferred embodiment, mA is calculated to minimize exposure time. Minimizing exposure time also minimizes patient motion. The smallest focal spot is chosen to minimize blur in the focal spot. However, a larger mA typically produces a bigger focal spot.

The control module 260 receives information from the user interface 230, image segmentation module 240, and characterization module 250. The control module 260 adjusts first and second exposure settings of the dual energy medical imaging system 210 with detector 220 to minimize energy dosage (such as x-ray energy dosage) and optimize image quality. The control module 260 adjusts the first exposure settings based on default settings for the input configuration information from the user interface 230. The control module 260 adjusts the second exposure settings based on the characterized image segment 320 from the image segmentation module 240 and characterization module 250. The control module 260 may adjust the desired kVp, mAs, and mA of the next exposure based on calculations from the image segmentation module 240 and characterization module 250. The control module 260 may also adjust focal spot size, dose set point, detector gain, detector readout timing, and the like. The control module 260 compares the second image with the first image to separate bone from soft tissue. An output displays and/or stores the resulting image.

An alternative embodiment acquires a very low dose "scout view" image taken initially at very low dose and potentially at very high x-ray energy (kVp). The scout image is preferably used to position the patient, but the scout image may also be used as the first exposure image input into the segmentation algorithm for analysis. The scout image comprises sufficient information to allow the segmentation algorithm and characterization algorithm to analyze the image.

An alternative embodiment adjusts exposure settings for each exposure based on a very low dose pre-shot image. Another embodiment adjusts exposure settings of n images based on the (n−1)th image. For example, an alternative embodiment involves triple energy imaging.

As an example, a lung x-ray may be taken using a preferred embodiment of the present invention. An x-ray technician configures the system 200 for the lung using the user interface 230. The patient 205 is positioned in view of the detector 220. An initial image 300 of the patient 205 is acquired by the dual energy medical imaging system 210 with the detector 220. The initial image 300 of the patient 205 is transmitted to the image segmentation module 230. The image segmentation module identifies the segment 320 of the patient image 310 that depicts the lung of the patient 205. The lung segment 320 is transmitted to the characterization module 250. The characterization module 250 may compare the lung segment 320 image data to average lung image attenuation data. The characterization module 250 may also correlate lung segment 320 image data with normalized patient lung data (e.g., calculate the difference between lung segment 320 image data and normalized patient lung data).

Image acquisition parameters for the second exposure are set based upon the characterization of the lung segment 320. For example, the second exposure may be adjusted based on the attenuation of the lung segment 320. Also, the second exposure of the patient 205 may be adjusted based on the difference between the lung segment 320 image data and the normalized patient lung data. The dual energy medical imaging system 210 performs a second exposure of the patient 205 using the updated image acquisition parameters. The detector 220 acquires an image from the second exposure. The control module 260 analyzes the first and second images to produce a resulting image separating bone and soft tissue. The resulting image is displayed on a screen for viewing by a doctor. The image of the patient's ribs may be separated from the soft tissue of the patient's lungs. Lung cancer nodules in the patient's lung are visible against the soft tissue. In a preferred embodiment, the time between the first and second exposures is at most one second.

Thus, the preferred embodiments of the present invention provide a fairly simple solution to identify serious medical conditions at an early stage while minimizing x-ray dosage to a patient. The medical diagnostic method and apparatus to control dual energy exposure techniques based on image information may improve the design of new medical imaging systems and may improve the diagnostic accuracy of existing medical imaging systems through anatomy-based exposure adjustment. The method and apparatus may be easily implemented and do not necessarily require a change to existing detector hardware.

While the invention has been described with reference to a preferred embodiment, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A method for controlling dual energy image acquisition to automatically adjust exposure parameters, said method comprising:

obtaining a first image from a first exposure of a patient, said first image including pixel values representative of a patient anatomy;

segmenting said first image based on said pixel values representative of the anatomy of the patient;

defining a set of patient parameters characterizing the patient anatomy in at least one segmented portion of said first image; and adjusting exposure settings for a second exposure of the patient anatomy based upon said set of patient parameters.

2. The method of claim 1, further comprising manually selecting an anatomy of interest to be located in said segmented portion.

3. The method of claim 1, further comprising obtaining a second image from said second exposure.

4. The method of claim 1, wherein said first exposure comprises a low dose x-ray positioning exposure.

5. The method of claim 1, wherein said set of patient parameters comprises attenuation of said representative anatomy.

6. The method of claim 1, wherein said set of patient parameters comprises normalized patient data.

7. The method of claim 1, wherein said set of patient parameters comprises a mathematical model of said representative anatomy.

8. The method of claim 1, wherein said set of patient parameters comprises bright and dark regions of said representative anatomy.

9. The method of claim 1, further comprising outputting a resulting anatomy image from an analysis of said first and second images.

10. The method of claim 9, wherein said analysis comprises separating said first and second images to produce the resulting anatomy image.

11. The method of claim 1, wherein said method may be executed in a maximum time of one second.

12. The method of claim 1, further comprising obtaining a preshot image, wherein exposure settings for said first and second exposures are adjusted based on said preshot image.

13. A system for controlling dual energy image acquisition, said system comprising:

a dual energy medical imaging apparatus for performing a select one of multiple exposure dosage levels and techniques, said dual energy medical imaging system acquiring at least first and second exposures;

a detector converting said first and second exposures into first and second digital images;

a user interface setting image acquisition parameters;

an image segmentation module identifying an anatomy of interest in said first digital image;

a characterization module defining a set of patient parameters characterizing said anatomy of interest; and a control module adjusting at least one of said exposure dosage levels and techniques performed by said dual energy image apparatus during said second exposure based on said set of patient parameters.

14. The system of claim 13, wherein said set of patient parameters comprises attenuation of a representative anatomy.

15. The system of claim 13, wherein said set of patient parameters comprises normalized patient data.

16. The system of claim 13, wherein said set of patient parameters comprises a mathematical model of a representative anatomy.

17. The system of claim 13, wherein the set of patient parameters comprises bright and dark areas of a representative anatomy.

18. The system of claim 13, wherein said dual energy medical imaging system adjusts for a low dose positioning exposure.

19. The system of claim 13, wherein said exposure energy comprises x-ray energy.

20. The system of claim 13, wherein said control module further constructs a resulting anatomy image based upon said at least first and second exposures.

21. The system of claim 13, wherein said control module further constructs a resulting anatomy image based upon separation of said at least first and second exposures.

22. The system of claim 13, further comprising an output, said output displaying a resulting anatomy image.

23. The system of claim 13, wherein said dual energy medical imaging system obtains a preshot image and adjusts a first exposure dosage level and a second exposure dosage level based on said preshot image.

24. A method for controlling multiple exposure image acquisition, said method comprising:

obtaining an image from an exposure of a patient, said image including pixel values representative of a patient anatomy;

segmenting said image based on said pixel values representative of the anatomy of the patient;

defining a set of patient parameters characterizing the patient anatomy in at least one segmented portion of said image;

adjusting exposure settings for a subsequent exposure of the patient anatomy based upon said set of patient parameters; and obtaining at least one subsequent exposures of the patient anatomy, each of said exposures obtained using exposure settings adjusted based on characterization of a previous image.

* * * * *